(12) United States Patent
Yoo et al.

(10) Patent No.: US 12,144,582 B2
(45) Date of Patent: Nov. 19, 2024

(54) MULTI DIAGNOSIS AND TREATMENT CATHETER AND CATHETER SYSTEM COMPRISING SAME

(71) Applicants: IUCF-HYU (INDUSTRY-UNIVERSITY COOPERATION FOUNDATION HANYANG UNIVERSITY), Seoul (KR); CHUNG-ANG UNIVERSITY INDUSTRY-ACADEMY COOPERATION FOUNDATION, Seoul (KR); KOREA UNIVERSITY RESEARCH AND BUSINESS FOUNDATION, Seoul (KR); KOREA ADVANCED INSTITUTE OF SCIENCE AND TECHNOLOGY, Daejeon (KR)

(72) Inventors: Hong Ki Yoo, Seoul (KR); Min Woo Lee, Suwon-si (KR); Jin Won Kim, Seoul (KR); Wang Yuhl Oh, Daejeon (KR); Kyeong Soon Park, Anseong-si (KR)

(73) Assignees: IUCF-HYU (INDUSTRY-UNIVERSITY COOPERATION FOUNDATION HANYANG UNIVERSITY), Seoul (KR); CHUNG-ANG UNIVERSITY INDUSTRY-ACADEMY COOPERATION FOUNDATION, Seoul (KR); KOREA ADVANCED INSTITUTE OF SCIENCE AND TECHNOLOGY, Daejeon (KR); Korea University Research and Business Foundation, Seoul (KR)

( * ) Notice: Subject to any disclaimer, the term of this patent is extended or adjusted under 35 U.S.C. 154(b) by 476 days.

(21) Appl. No.: 17/602,419

(22) PCT Filed: Apr. 3, 2020

(86) PCT No.: PCT/KR2020/004537
§ 371 (c)(1),
(2) Date: Oct. 8, 2021

(87) PCT Pub. No.: WO2020/209545
PCT Pub. Date: Oct. 15, 2020

(65) Prior Publication Data
US 2022/0167849 A1    Jun. 2, 2022

(30) Foreign Application Priority Data

Apr. 8, 2019    (KR) ........................ 10-2019-0040521

(51) Int. Cl.
*A61B 5/00*    (2006.01)
*F21V 8/00*    (2006.01)

(52) U.S. Cl.
CPC .......... *A61B 5/0036* (2018.08); *A61B 5/0084* (2013.01); *A61B 5/6852* (2013.01); *G02B 6/0008* (2013.01)

(58) Field of Classification Search
CPC .......... A61B 2018/2244; A61B 5/0036; A61B 5/0084; A61B 5/6852; A61B 1/00165;
(Continued)

(56) References Cited

U.S. PATENT DOCUMENTS

| | | | | | |
|---|---|---|---|---|---|
| 4,134,642 | A | * | 1/1979 | Kapron | G02B 6/4469 385/127 |
| 4,314,740 | A | * | 2/1982 | Bickel | G02B 6/2817 385/127 |

(Continued)

FOREIGN PATENT DOCUMENTS

| | | |
|---|---|---|
| JP | 6236386 B2 | 11/2017 |
| JP | 2018-029067 A | 2/2018 |

(Continued)

OTHER PUBLICATIONS

Lee [Development of Intravascular Optical Theranostic Catheter System for Cardiovascular Disease, Annual Biophotonics conference 2018]. (Year: 2018).*

(Continued)

*Primary Examiner* — Oommen Jacob
(74) *Attorney, Agent, or Firm* — Sughrue Mion, PLLC

(57) ABSTRACT

Disclosed are a catheter which can perform both multi diagnosis and treatment, and a catheter system comprising
(Continued)

same. A multi diagnosis and treatment catheter comprises: a triple-clad fiber; and a lens connected to one end of the triple-clad fiber. The triple-clad fiber comprises: a core guiding a first diagnostic light; a first cladding surrounding the core and guiding a second diagnostic light; a second cladding surrounding the first cladding; a third cladding surrounding the second cladding and guiding a therapeutic light; and a coating layer surrounding the third cladding.

2 Claims, 3 Drawing Sheets

(58) Field of Classification Search
CPC ...... G02B 6/0008; G02B 6/3624; A61N 5/06; A61N 5/0603; A61N 2005/063
See application file for complete search history.

(56) References Cited

U.S. PATENT DOCUMENTS

| | | | | |
|---|---|---|---|---|
| 4,641,917 | A * | 2/1987 | Glodis | G02B 6/03655 385/127 |
| 4,715,695 | A * | 12/1987 | Nishimura | G02B 6/0365 385/127 |
| 4,938,205 | A * | 7/1990 | Nudelman | G02B 23/26 257/E31.115 |
| 4,986,629 | A * | 1/1991 | Auge | G02B 6/03644 385/127 |
| 5,044,724 | A * | 9/1991 | Glodis | C03B 37/01211 385/127 |
| 5,295,143 | A * | 3/1994 | Rao | H01S 3/2383 359/328 |
| 5,721,800 | A * | 2/1998 | Kato | G02B 6/02285 385/127 |
| 6,442,319 | B1 * | 8/2002 | Dietz | G01N 21/7703 385/122 |
| 6,514,277 | B1 * | 2/2003 | Lilge | A61N 5/0601 600/478 |
| 6,625,364 | B2 * | 9/2003 | Johnson | G02B 6/02304 385/127 |
| 7,120,481 | B2 * | 10/2006 | Keller | A61B 5/6864 600/339 |
| 7,437,046 | B2 * | 10/2008 | DiGiovanni | G02B 6/2804 385/128 |
| 8,591,087 | B2 * | 11/2013 | Bickham | G02B 6/02347 362/558 |
| 8,764,666 | B2 * | 7/2014 | Chen | A61B 8/12 600/459 |
| 8,781,269 | B2 * | 7/2014 | Huber | G02B 6/3508 385/18 |
| 9,557,154 | B2 | 1/2017 | Tearney et al. | |
| 9,561,078 | B2 * | 2/2017 | Seibel | A61B 1/0017 |
| 9,844,318 | B2 * | 12/2017 | Parto | A61F 9/00821 |
| 9,968,261 | B2 | 5/2018 | Motafakker-Fard et al. | |
| 2002/0001444 | A1 * | 1/2002 | Hirano | G02B 6/03666 385/127 |
| 2002/0041723 | A1 * | 4/2002 | Ronnekleiv | A61B 5/0084 385/12 |
| 2003/0189456 | A1 * | 10/2003 | Foster | G01N 21/64 327/393 |
| 2004/0225222 | A1 * | 11/2004 | Zeng | G01J 3/32 600/476 |
| 2006/0013544 | A1 * | 1/2006 | Bouma | G02B 6/02042 385/116 |
| 2006/0215976 | A1 * | 9/2006 | Singh | G02B 6/02042 385/124 |
| 2007/0060804 | A1 * | 3/2007 | Thompson | A61B 5/0071 607/1 |
| 2007/0135874 | A1 * | 6/2007 | Bala | A61N 5/0603 607/94 |
| 2007/0274650 | A1 * | 11/2007 | Tearney | A61B 1/00082 385/118 |
| 2009/0024191 | A1 * | 1/2009 | Seibel | A61B 18/22 600/478 |
| 2010/0228119 | A1 * | 9/2010 | Brennan | A61B 5/6852 600/424 |
| 2011/0033156 | A1 * | 2/2011 | Sanghera | B29D 11/00682 264/2.7 |
| 2011/0205349 | A1 * | 8/2011 | Li | G02B 6/03611 348/E7.085 |
| 2012/0123205 | A1 * | 5/2012 | Nie | A61B 5/0084 600/109 |
| 2013/0144165 | A1 * | 6/2013 | Ebbini | G01S 7/52046 600/439 |
| 2013/0329224 | A1 * | 12/2013 | Takaoka | A61B 1/0669 356/402 |
| 2014/0268168 | A1 * | 9/2014 | Feldman | G02B 23/2484 356/479 |
| 2015/0043597 | A1 * | 2/2015 | Yusim | G02B 6/29382 372/6 |
| 2015/0272442 | A1 * | 10/2015 | Motafakker-Fard | G01N 21/474 600/478 |
| 2016/0045102 | A1 * | 2/2016 | Yu | A61B 5/0062 600/427 |
| 2016/0245990 | A1 * | 8/2016 | Boyden | A61N 5/0601 |
| 2018/0081165 | A1 | 3/2018 | Schultheis et al. | |
| 2018/0303327 | A1 * | 10/2018 | Yamada | A61B 5/0066 |
| 2020/0123053 | A1 * | 4/2020 | Shih | C03C 25/68 |
| 2020/0305732 | A1 * | 10/2020 | Xu | A61B 5/0084 |
| 2021/0106233 | A1 * | 4/2021 | Sherlock | G02B 21/0056 |
| 2022/0167849 | A1 * | 6/2022 | Yoo | A61N 5/06 |

FOREIGN PATENT DOCUMENTS

| | | |
|---|---|---|
| KR | 10-2013-0006630 A | 1/2013 |
| KR | 10-1622053 B1 | 5/2016 |
| KR | 10-1808675 B1 | 1/2018 |

OTHER PUBLICATIONS

Lee, Min Woo et al., Development of intravascular optical theranostic catheter system for cardiovascular disease, Annual Biophotonics Conference 2018(Oct. 26, 2018), See entire main text. *This document is a document declared as an exception to lack of novelty in an earlier application that servers as a basis for claiming priority of the present international application.
International Search Report for PCT/KR2020/004537 dated Nov. 13, 2020.
Written Opinion for PCT/KR2020/004537 dated Nov. 13, 2020.

* cited by examiner

MULTI DIAGNOSIS AND TREATMENT CATHETER AND CATHETER SYSTEM COMPRISING SAME

CROSS-REFERENCE TO RELATED APPLICATIONS

This application is a National Phase application of PCT International Application No. PCT/KR2020/004537, which was filed on Apr. 3, 2020, and which claims priority from Korean Patent Application No. 10-2019-0040521 filed on Apr. 8, 2019. The disclosure of the above patent application is incorporated herein by reference in their entirety.

BACKGROUND

Technical Field

The present disclosure relates to a multi-diagnostic and therapeutic catheter and a catheter system including the same, and more particularly, to a catheter capable of performing both diagnosis and treatment and a catheter system including the same.

Background Art

Research based on one or more imaging techniques, such as intravascular optical coherence tomography (IVOCT), IVOCT/near-infrared fluorescence (IVOCT/NIRF) imaging, IVOCT/near-infrared autofluorescence (IVOCT/NIRAF) imaging, IVOCT/near-infrared spectroscopy (IVOCT/NIRS), IVOCT/fluorescence lifetime imaging microscopy (IVOCT/FLIm), and the like is being actively conducted in which a catheter is inserted into tubular tissue such as a blood vessel, digestive system, urethra, etc. to image the inside of the tissue and make a diagnosis based on images.

In addition, in order to apply treatment methods using light, such as photodynamic therapy (PDT), photothermal therapy (PTT), photocoagulation, low-level laser therapy (LLLT), and the like, to the treatment of tubular tissue, therapeutic catheters using optical fibers are being developed and sold.

Recently, research on catheters capable of performing both diagnosis and treatment is being conducted.

DISCLOSURE

Technical Problem

The present disclosure is directed to providing a catheter capable of performing both diagnosis and treatment and a catheter system including the same.

In particular, the present disclosure is directed to providing a catheter capable of performing both multi-diagnosis and treatment and a catheter system including the same.

Technical Solution

An aspect of the present disclosure provides a multi-diagnostic and therapeutic catheter including a triple-clad fiber and a lens coupled to one end of the triple-clad fiber, wherein the triple-clad fiber includes a core configured to guide first diagnostic light, a first cladding configured to surround the core and guide second diagnostic light, a second cladding configured to surround the first cladding, a third cladding configured to surround the second cladding and guide therapeutic light, and a coating layer configured to surround the third cladding.

Another aspect of the present disclosure provides a multi-diagnostic and therapeutic catheter including a triple-clad fiber configured to guide first diagnostic light, second diagnostic light, and therapeutic light and a lens coupled to one end of the triple-clad fiber, wherein the triple-clad fiber includes a core, a first cladding configured to surround the core, a second cladding configured to surround the first cladding, a third cladding configured to surround the second cladding, and a coating layer configured to surround the third cladding, and the first diagnostic light, the second diagnostic light, and the therapeutic light are respectively guided through the core, the first cladding, and the third cladding with the second cladding as a boundary and having the smallest refractive index among the core and the first to third claddings.

Still another aspect of the present disclosure provides a multi-diagnostic and therapeutic catheter system including a first diagnostic light source, a second diagnostic light source, a therapeutic light source, a triple-clad fiber configured to guide light of the first diagnostic light source, light of the second diagnostic light source, and light of the therapeutic light source and including a core, a first cladding, a second cladding, a third cladding, and a coating layer, and a lens coupled to one end of the triple-clad fiber.

Advantageous Effects

According to an embodiment of the present disclosure, it is possible to simultaneously guide diagnostic light and therapeutic light on the basis of different imaging techniques, and thus it is possible for one catheter to perform both multi-diagnosis and treatment.

Further, according to an embodiment of the present disclosure, by allowing multiple diagnostic lights and therapeutic light to be guided through a core and first and third claddings with a second cladding of a triple-clad fiber as a boundary, light loss can be minimized.

MODES OF THE DISCLOSURE

While the present disclosure is open to various modifications and alternative forms, specific embodiments thereof are shown by way of example in the accompanying drawings and will herein be described in detail. However, it should be understood that there is no intent to limit the present disclosure to the particular forms disclosed, and on the contrary, the disclosure is to cover all modifications, equivalents, and alternatives falling within the spirit and scope of the present disclosure. Like numbers refer to like elements throughout the description of the figures.

As described above, techniques in which both single diagnosis and treatment may be performed with one catheter are being developed. The diseases that can be diagnosed are different depending on imaging techniques. Therefore, when a catheter capable of performing both multi-diagnosis and treatment on the basis of a plurality of imaging techniques is developed, it is possible to perform treatment based on a more accurate diagnosis result.

The present disclosure has been developed with the above idea and embodiments of the present disclosure are for providing a catheter capable of performing both multi-diagnosis and treatment using a triple-clad fiber (TCF) and a catheter system. A TCF serves as a channel through which diagnostic light and therapeutic light used in different imaging techniques may move. Therefore, according to an embodiment of the present disclosure, both multi-diagnosis and treatment may be performed.

Hereinafter, embodiments of the present disclosure will be described in detail with reference to the accompanying drawings.

Figure 1:
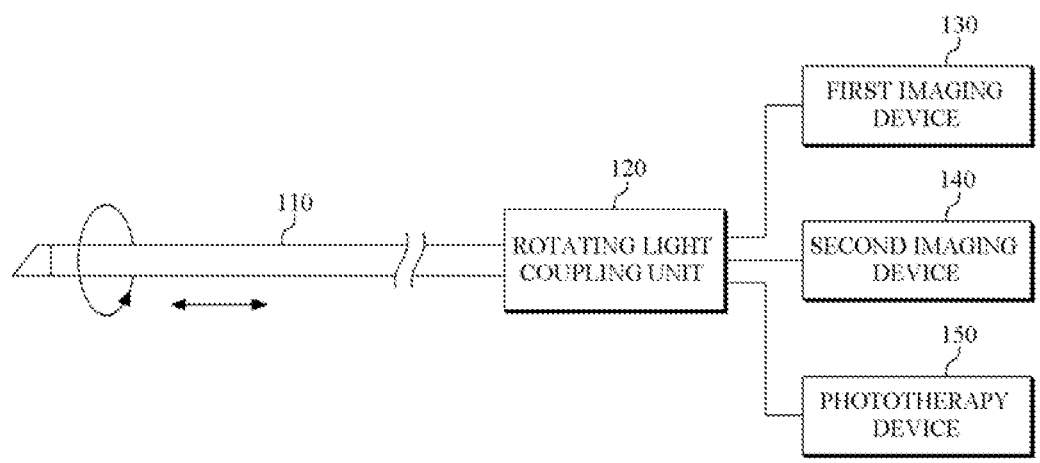
FIG. 1 is a drawing for describing a multi-diagnostic and therapeutic catheter system according to an embodiment of the present disclosure.

FIG. 1 is a drawing for describing a multi-diagnostic and therapeutic catheter system according to an embodiment of the present disclosure.

Referring to FIG. 1, the multi-diagnostic and therapeutic catheter system according to the embodiment of the present disclosure includes a multi-diagnostic and therapeutic catheter 110, a rotating light coupling unit 120, a first imaging device 130, a second imaging device 140, and a phototherapy device 150.

The multi-diagnostic and therapeutic catheter 110 is inserted into a lesion site, such as a blood vessel or the like, of a patient and guides first diagnostic light and second diagnostic light provided from the first and second imaging devices 130 and 140 to irradiate the lesion site of the patient with the first diagnostic light and the second diagnostic light. The diagnostic light radiated to the lesion site is reflected by the lesion site and the multi-diagnostic and therapeutic catheter 110 provides the reflected light to the first and second imaging devices 130 and 140. Further, the multi-diagnostic and therapeutic catheter 110 guides therapeutic light provided from the phototherapy device 150 to irradiate the lesion site of the patient with the therapeutic light.

The multi-diagnostic and therapeutic catheter 110 may guide the diagnostic light and the therapeutic light by using a TCF including a core, first to third claddings, and a coating layer. The multi-diagnostic and therapeutic catheter 110 will be described in more detail with reference to FIGS. 2 to 4.

The first and second imaging devices 130 and 140 include first and second diagnostic light sources, respectively, and provide pieces of light of the first and second diagnostic light sources to the multi-diagnostic and therapeutic catheter 110. Then, an image of the lesion site is generated using the light reflected by the lesion site.

In an embodiment, the first and second imaging devices 130 and 140 may be imaging devices based on imaging techniques such as optical coherence tomography (OCT)/near-infrared fluorescence (NIRF) imaging, OCT/near-infrared autofluorescence (NIRAF) imaging, OCT/fluorescence lifetime imaging microscopy (FLIm), and the like. In addition to the above imaging techniques, a combination of various imaging techniques may be applied according to the embodiment.

The phototherapy device 150 includes a therapeutic light source and provides light of the therapeutic light source to the multi-diagnostic and therapeutic catheter 110. In an embodiment, the phototherapy device 150 may be a device based on one of phototherapy techniques such as photodynamic therapy (PDT), photothermal therapy (PTT), photocoagulation, low-level laser therapy (LLLT), and the like. In addition to the above phototherapy techniques, various phototherapy techniques may be applied according to the embodiment.

The rotating light coupling unit 120 couples the first and second imaging devices 130 and 140, the phototherapy device 150, and the multi-diagnostic and therapeutic catheter 110 and rotates the multi-diagnostic and therapeutic catheter 110 at high speed or moves the multi-diagnostic and therapeutic catheter 110 in forward and backward directions. By the operation of the rotating light coupling unit 120, the multi-diagnostic and therapeutic catheter 110 may irradiate not only the lesion site with the diagnostic light but also the lesion site with the therapeutic light while moving the inserted portion thereof.

According to an embodiment of the present disclosure, it is possible to simultaneously guide diagnostic light based on different imaging techniques and therapeutic light, and thus it is possible for one catheter to perform both multi-diagnosis and treatment.

Figure 2:
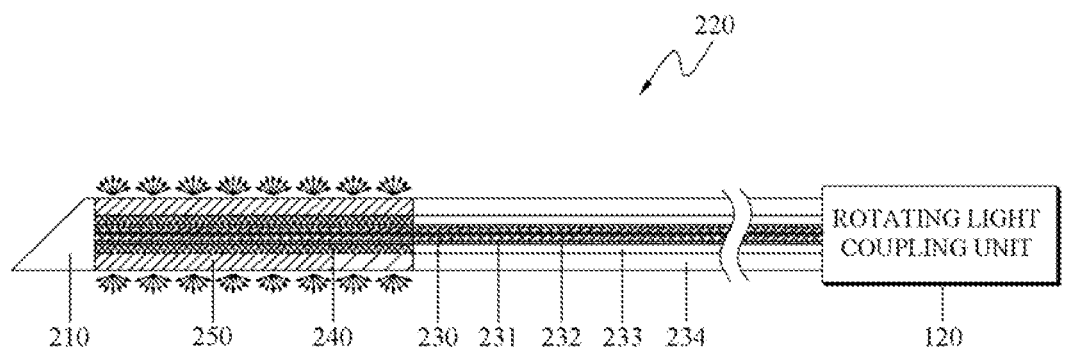
FIGS. 2 and 3 are drawing s for describing a multi-diagnostic and therapeutic catheter according to an embodiment of the present disclosure.
Figure 3:
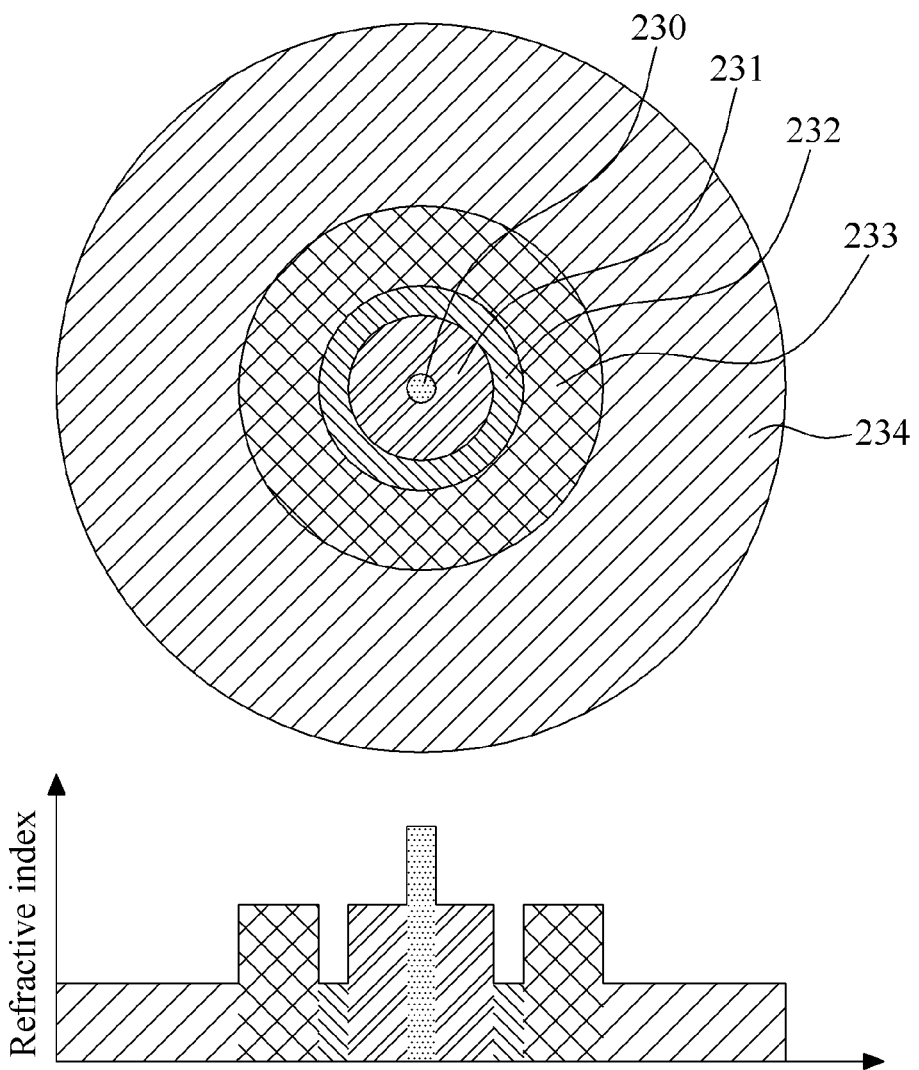

FIGS. 2 and 3 are drawings for describing a multi-diagnostic and therapeutic catheter according to an embodiment of the present disclosure, wherein FIG. 2 is a cross-sectional view of the multi-diagnostic and therapeutic catheter and FIG. 3 is a view for describing a refractive index of a TCF.

A multi-diagnostic and therapeutic catheter 110 according to the embodiment of the present disclosure includes a lens 210 and a TCF 220.

The lens 210 is coupled to one end of the TCF 220 and collects first diagnostic light and second diagnostic light guided through the TCF 220 to irradiate a specimen such as a lesion site with the first diagnostic light and the second diagnostic light. In an embodiment, a ball lens may be used.

The TCF 220 includes a core 230, first to third claddings 231, 232, and 233, and a coating layer 234. The second cladding 232 surrounds the first cladding 231 surrounding the core 230 and the coating layer 234 surrounds the third cladding 233 surrounding the second cladding 232.

In an embodiment, the first diagnostic light may be guided through the core 230 and the second diagnostic light may be guided through the first cladding 231. Therapeutic light may be guided through the third cladding 233.

As illustrated in FIG. 3, with respect to a refractive index of the TCF 220 according to the embodiment of the present disclosure, a refractive index of the first cladding 231 is smaller than a refractive index of the core 230 having a maximum refractive index and greater than a refractive index of the second cladding 232, and a refractive index of the third cladding 233 is greater than the refractive index of the second cladding 232 and greater than a refractive index of the coating layer 234. Therefore, the diagnostic light and the therapeutic light may be totally reflected by the core 230, the first and third claddings 231 and 233 and may move.

The refractive index of the second cladding 232 is smaller than the refractive indexes of the first and third claddings 231 and 233 adjacent thereto such that it is difficult for total reflection to occur in the second cladding 232. Therefore, when light is guided through the second cladding 232, the light may leak to the first cladding 231 or third cladding 233 adjacent thereto, thereby reducing light efficiency. Accordingly, in an embodiment of the present disclosure, the second cladding 232 is not used as a channel through which light moves, and the first and third claddings 231 and 233, which are separated by the second cladding 232, and the core 230 are used as channels through which light moves.

In some embodiments, except for the second cladding 232 and the coating layer 234, each of the core 230, the first cladding 231, and the third cladding 233 may be used as a channel for diagnostic light or therapeutic light. In other words, the first diagnostic light, the second diagnostic light, and the therapeutic light may be respectively guided through the core 230, the first cladding 231, and the third cladding 233 with the second cladding 232 as a boundary and having the smallest refractive index among the core 230 and the first to third claddings 231, 232, and 233. As will be described below, in the embodiment of FIG. 2, a structure in which the therapeutic light is radiated through an outer periphery of the third cladding 233 is used, and thus the therapeutic light may be guided through the third cladding 233.

Referring to FIG. 2 again, the coating layer may not be formed in some regions of the third cladding 233 such that the therapeutic light is radiated to a lesion site through the outer periphery of the third cladding 233. That is, the coating layer may surround remaining portions of the outer periphery other than the outer periphery of the third cladding 233 to which the therapeutic light is radiated. The outer periphery of the third cladding 233 to which the therapeutic light is radiated may start from one end of the lens 210, that is, a coupling surface of the lens 210 and the TCF 220, and a length of the outer periphery may be variously determined according to the embodiment.

Meanwhile, the third cladding 233 includes a scattering pattern 240 formed on the outer periphery thereof, and the coating layer is not formed in a region in which the scattering pattern 240 is formed, as described above. A transparent tube 250 through which light passes surrounds the region, in which the scattering pattern is formed and the coating layer is not formed, and protects the third cladding 233.

As described above, according to the embodiment of the present disclosure, the multiple diagnostic lights and the therapeutic light may be simultaneously guided through the catheter and the multiple diagnostic lights and the therapeutic light are guided through the core and the first and third claddings with the second cladding as a boundary, thereby minimizing light loss.

Figure 4:
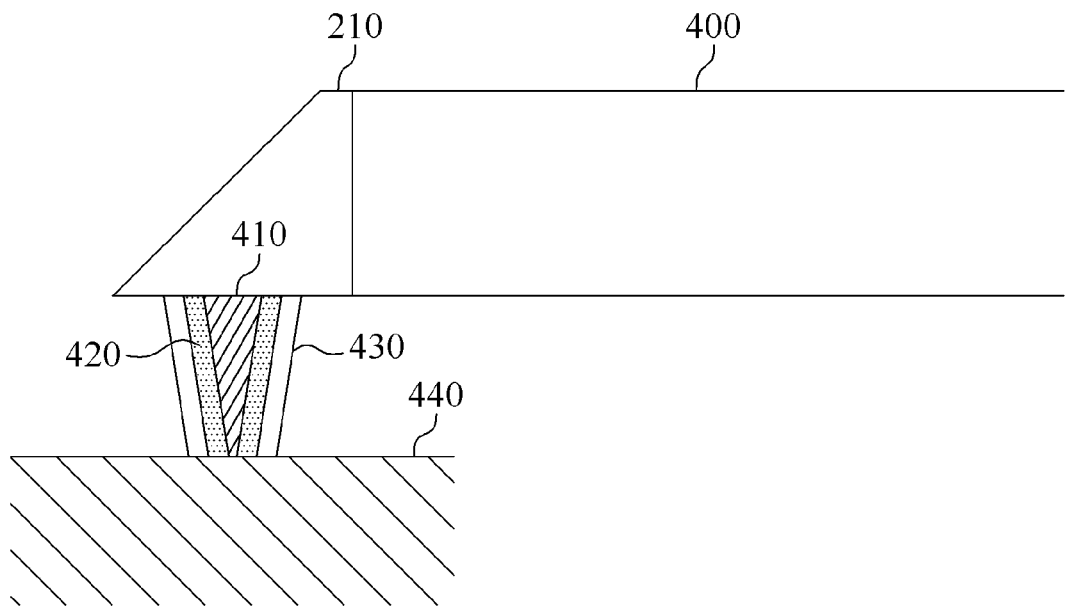
FIG. 4 is a drawing for describing a multi-diagnostic and therapeutic catheter according to another embodiment of the present disclosure.

FIG. 4 is a drawing for describing a multi-diagnostic and therapeutic catheter according to another embodiment of the present disclosure.

Unlike the multi-diagnostic and therapeutic catheter as described in FIG. 2, in the multi-diagnostic and therapeutic catheter of FIG. 4, a scattering pattern is not formed on an outer periphery of a third cladding of a TCF 400 and a coating layer surrounds the entirety of the outer periphery of the third cladding.

In the multi-diagnostic and therapeutic catheter, therapeutic light 430 may not be radiated to a lesion site 440 through the outer periphery of the third cladding but may be radiated to the lesion site 440 through a lens 210 together with first diagnostic light 410 and second diagnostic light 420.

As described above, according to another embodiment of the present disclosure, the therapeutic light may not be guided through the third cladding but may be guided through a core. That is, since the therapeutic light may not be radiated to the lesion site through the outer periphery of the third cladding, the therapeutic light may move through various paths that may be totally reflected, other than the third cladding. Similarly, first diagnostic light may not be guided through the core but may be guided through the third cladding.

Eventually, the paths through which the diagnostic light and the therapeutic light are guided may vary according to the method of irradiating the therapeutic light. According to an embodiment of the present disclosure, each of the first diagnostic light and the second diagnostic light and therapeutic light may be guided through one of various paths selected from among the core, a first cladding, and the third cladding.

Figure 5:
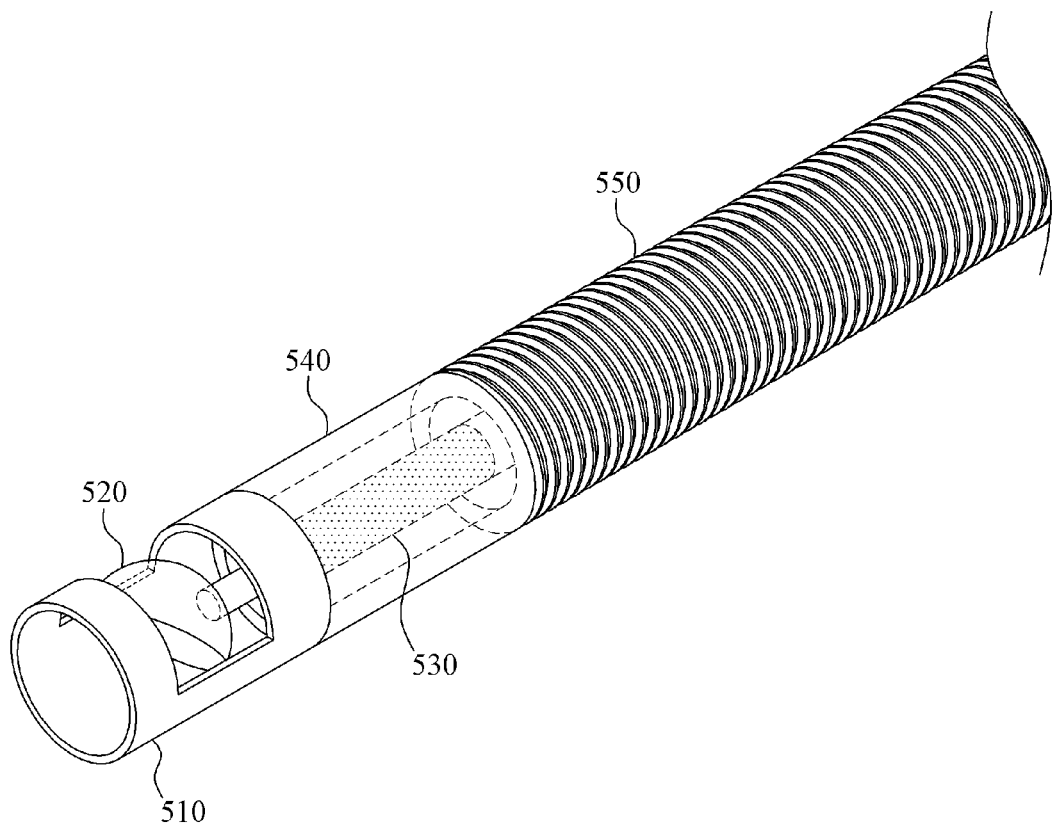
FIG. 5 is a drawing for describing a multi-diagnostic and therapeutic catheter according to a specific embodiment of the present disclosure.

FIG. 5 is a drawing for describing a multi-diagnostic and therapeutic catheter according to a specific embodiment of the present disclosure.

Referring to FIG. 5, the multi-diagnostic and therapeutic catheter according to the embodiment of the present disclosure includes a hypotube 510, a ball lens 520, first and second tubes 530 and 540, a TCF, and a torque coil 550.

The hypotube 510 protects the ball lens 520 and the second tube 540 protects a region to which therapeutic light is radiated. The second tube 540 may be coupled to the hypotube 510 and the torque coil 550 and may be provided to be spaced apart from the first tube 530. The first tube 530 surrounds a third cladding of the TCF to which the therapeutic light is radiated, and the therapeutic light is radiated through the first tube 530. Like the first tube 530, the second tube 540 is also transparent, and thus the therapeutic light may be radiated to a specimen. The torque coil 550 surrounds the TCF and transmits torque for rotation of the multi-diagnostic and therapeutic catheter.

While the present disclosure has been described with reference to specific details such as detailed components, specific embodiments and drawings, these are only examples to facilitate overall understanding of the present disclosure and the present disclosure is not limited thereto. It will be understood by those skilled in the art that various modifications and alterations may be made. Therefore, the spirit and scope of the present disclosure are defined not by the detailed description of the present disclosure but by the appended claims, and encompasses all modifications and equivalents that fall within the scope of the appended claims.

What is claimed is:

1. A multi-diagnostic and therapeutic catheter comprising:
    a triple-clad fiber;
    a lens coupled to one end of the triple-clad fiber; and
    a transparent tube,
    wherein the triple-clad fiber includes:
        a core configured to guide first diagnostic light;
        a first cladding configured to surround the core and including an outer periphery configured to guide second diagnostic light;
        a second cladding configured to surround the first cladding;
        a third cladding configured to surround the second cladding and guide therapeutic light; and
        a coating layer configured to surround the third cladding,
    wherein the third cladding includes a scattering pattern formed on an outer periphery thereof, and
    wherein the transparent tube is configured to surround a region in which the scattering pattern is formed and the coating layer is not formed.

2. The multi-diagnostic and therapeutic catheter of claim 1, wherein:
    the first cladding has a refractive index which is smaller than a refractive index of the core having a maximum refractive index and greater than a refractive index of the second cladding; and the third cladding has a refractive index which is greater than the refractive index of the second cladding and greater than a refractive index of the coating layer.

\* \* \* \* \*